US00PP21214P2

(12) United States Plant Patent
Skotak

(10) Patent No.: US PP21,214 P2
(45) Date of Patent: Aug. 17, 2010

(54) *GUZMANIA* PLANT NAMED 'DURAODE'
(50) Latin Name: ***Guzmania×Vriesea* hybrid**
Varietal Denomination: Duraode

(76) Inventor: Chester Skotak, Apdo. 652, 4050 Alajuela (CR)

( * ) Notice: Subject to any disclaimer, the term of this patent is extended or adjusted under 35 U.S.C. 154(b) by 0 days.

(21) Appl. No.: 12/380,498

(22) Filed: Feb. 27, 2009

(51) Int. Cl.
*A01H 5/00* (2006.01)

(52) U.S. Cl. ..... Plt./371
(58) Field of Classification Search ..... Plt./371
See application file for complete search history.

*Primary Examiner*—Susan B McCormick Ewoldt

(57) ABSTRACT

A new and distinct *Guzmania×Vriesea* hybrid cultivar named 'Duraode' is disclosed, characterized by a unique inflorescence shape and color.

1 Drawing Sheet

Figure 1:
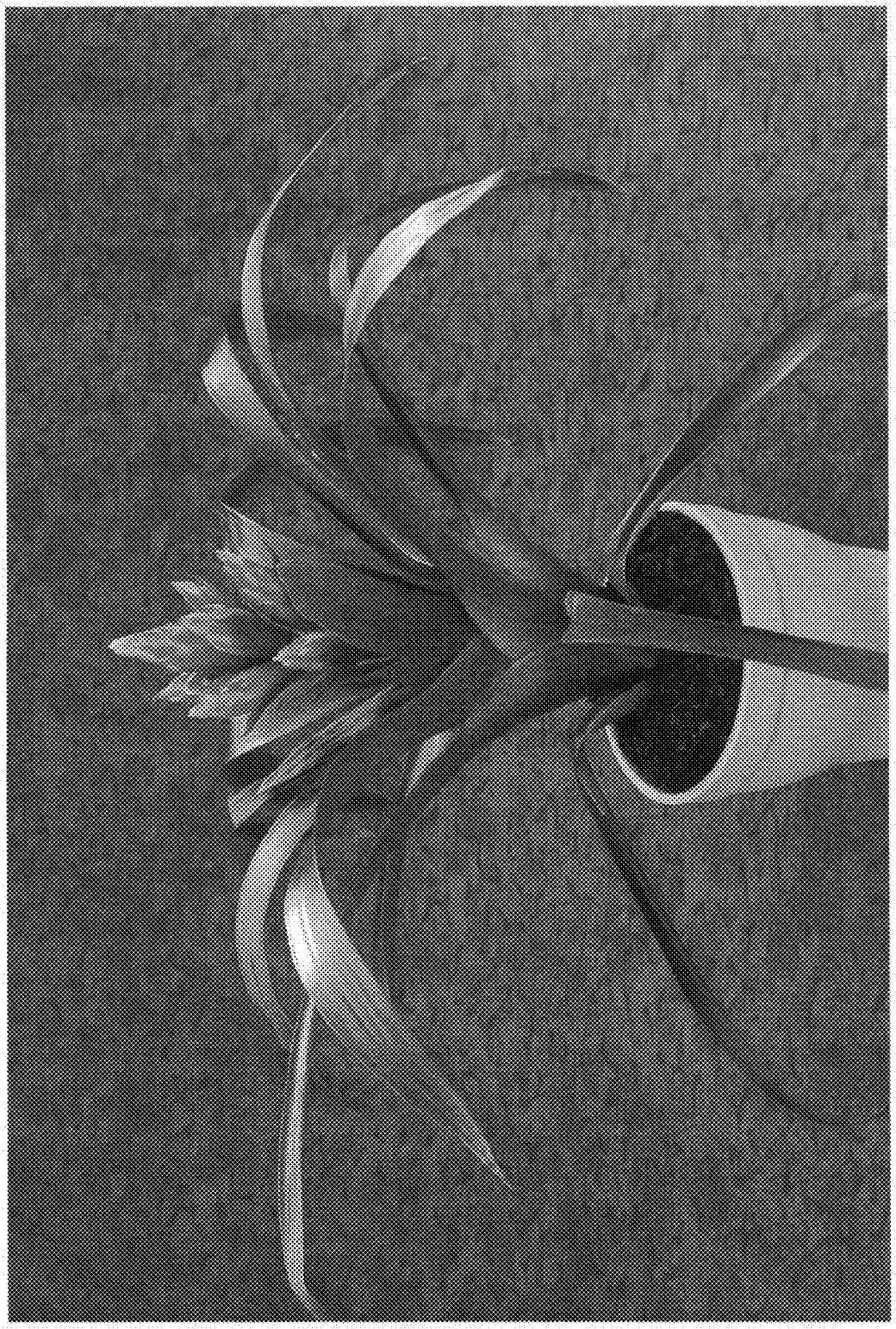

Latin name of the genus and species: *Guzmania×Vriesea* hybrid.

Variety denomination: 'Duraode'.

BACKGROUND OF THE INVENTION

The new cultivar is a product of a planned breeding program. The new variety originated from a cross pollination of the seed parent, *Guzmania lingulata×wittmackii* with the pollen parent, a Vriesea of unknown species, performed by the inventor in 1999.

It was discovered by the inventor, Chester Skotak Jr., a citizen of Costa Rica, in Ajauela, Costa Rica during October 2001, in a group of seedlings resulting from the 1999 crossing.

Asexual reproduction of the new cultivar 'Duraode' was first performed in Belgium by tissue culture in October 2004. 'Duraode' has since produced several generations by micropropagation and has shown that the unique features of this cultivar are stable and reproduced true to type.

SUMMARY OF THE INVENTION

The cultivar 'Duraode' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Duraode' These characteristics in combination distinguish 'Duraode' as a new and distinct *Guzmania×Vriesea* hybrid cultivar:

1. Unique inflorescence shape.
2. Unique inflorescence color.
3. Suitability as an indoor pot plant.

Plants of the new cultivar 'Duraode' are similar to both parent varieties in some horticultural characteristics. However, 'Duraode' differs from both the seed and pollen parents in having a different inflorescence shape.

COMMERCIAL COMPARISON

'Duraode' is best compared to the commercial variety *Guzmania* 'Patricia,' filed for US plant patent, with unknown serial number. Plants of 'Patricia' are similar to plants of 'Duraode' in most horticultural characteristics, however, 'Duraode' has a wider inflorescence, and has an inflorescence in three colors, red, orange and yellow, compared to an all red inflorescence of 'Patricia'.

BRIEF DESCRIPTION OF THE PHOTOGRAPH

The accompanying photograph in FIG. 1 illustrates in full color a typical plant of 'Duraode' grown in a greenhouse. This plant is approximately 2 years old, shown in an 12 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Duraode' plants grown in a climate controlled greenhouse in Evergem, the Netherlands. Temperatures ranged from 20° C. to 28° C. night and day. No artificial light, photoperiodic treatments or chemical treatments were given to the plants. Measurements and numerical values represent averages of typical plant types.

Botanical classification: *Guzmania×Vriesea* hybrid cultivar 'Duraode'.

PLANT

Growth habit: Upright, flattened sphere, forming compact rosettes around a single axis. One straight, upright inflorescence arising from the center of plant.
Height: Approximately 40.8 cm.
Plant spread: Approximately 49.4 cm in a 12 cm pot.
Normal pot size: 9, 11, 12 and 15 cm.
Growth rate: Moderate.
Branching characteristics: Upright, non-branching.
Number of leaves per stem: Approximately 29.
Age of plant described: Approximately 2 years.

FOLIAGE

Leaf:

*Arrangement.*—Whorled, single occurring basal rosettes.

*Average length.*—Approximately 25.4 cm.

*Average width.*—Average 4.0 cm, narrowest 3.6 cm, widest 4.3 cm.
*Shape of blade.*—Ligulate.
*Aspect.*—Slightly recurved.
*Apex.*—Apiculate.
*Base.*—Sheathing.
*Margin.*—Entire.
*Texture of top surface.*—Smooth, moderately glossy.
*Texture of bottom surface.*—Smooth, moderately glossy.
*Color.*—Young foliage upper side: Near RHS Green N137B, base lighter, near Yellow-green 146C. Young foliage under side: Near RHS Yellow-green 146A, base lighter, near Yellow-green 146C. Mature foliage upper side: Near RHS Green N137B, base lighter, near Yellow-green 146B. Mature foliage under side: Near RHS Yellow-green 146A, base lighter, near Yellow-green 146C.
*Venation.*—Type: Parallel. Venation coloration: Identical/Indistinguishable from foliage.

Petiole: Not present, sessile.

INFLORESCENCE

General description: Simple spike(scape) consisting of many bracts only. No individual flowers are visible. Spike emerges from the center of the rosette. Inflorescence is formed by conspicuous bracts.
*Inflorescence height(excluding peduncle.*—11 cm.
*Inflorescence width.*—19.3 cm.

Peduncle:
*Length.*—29.8 cm.
*Diameter.*—0.8 cm.
*Aspect.*—Very straight, 90° angle to rosette.
*Strength.*—Very strong.
*Color.*—Near RHS Yellow-green 145C.

Bracts:
*Shape.*—Ligulate.
*Length.*—Average 8.9 cm.
*Width.*—Average 2.6 cm.
*Tip.*—Acute.
*Base.*—Sheathed.
*Margin.*—Entire.
*Outermost bract coloration.*—Upperside: Near RHS Red 42B. Underside: Near RHS Red 45A.
*Innermost/interior bract coloration.*—Upperside: Not visible, fully attached. Underside: Near Orange-Red 32A. Outermost Tip: Near RHS Yellow-Orange-17B.
*Scape bract coloration.*—Upperside: Near RHS Yellow-green 144A, base Yellow-green 145B, slightly tinged Red 39B. Underside: Near RHS Yellow-green 146B, base Yellow-green 150D.

OTHER CHARACTERISTICS

Disease resistance: Neither resistance nor susceptibility to diseases or pests has been observed in this variety.
Drought tolerance and cold tolerance: Observed to tolerate temperatures to 40° C. without any negative effects. Temperature tolerance above this range has not been observed. Tolerance of cold temperatures has not been observed.
Fruit/seed production: Not observed.

What is claimed is:

1. A new and distinct cultivar of *Guzmania*×*Vriesea* hybrid plant named 'Duraode' as herein illustrated and described.

* * * * *